United States Patent
LaVon et al.

(10) Patent No.: US 10,462,750 B2
(45) Date of Patent: *Oct. 29, 2019

(54) SENSOR SYSTEMS FOR ABSORBENT ARTICLES COMPRISING SENSOR GATES

(71) Applicant: The Procter & Gamble Company, Cincinnati, OH (US)

(72) Inventors: Gary Dean LaVon, Liberty Township, OH (US); Grant Edward Anders Striemer, Fairfield Township, OH (US); Jonathan Livingston Joyce, Independence, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/296,329

(22) Filed: Mar. 8, 2019

(65) Prior Publication Data

US 2019/0208475 A1 Jul. 4, 2019

Related U.S. Application Data

(63) Continuation of application No. 14/455,088, filed on Aug. 8, 2014, now Pat. No. 10,292,112.
(Continued)

(51) Int. Cl.
*H04W 52/22* (2009.01)
*A61F 13/42* (2006.01)
(Continued)

(52) U.S. Cl.
CPC ....... *H04W 52/22* (2013.01); *A61F 13/15772* (2013.01); *A61F 13/42* (2013.01); *A61F 13/49* (2013.01); *A61F 2013/424* (2013.01)

(58) Field of Classification Search
None
See application file for complete search history.

(56) References Cited

U.S. PATENT DOCUMENTS 3,848,594 A 11/1974 Buell
3,860,003 A 1/1975 Buell
(Continued)

FOREIGN PATENT DOCUMENTS

EP 0 149 880 A2 5/1984
EP 149880 7/1985
(Continued)

OTHER PUBLICATIONS

Author: Federal Communication Commission; Title: Reassessment of Federal Communications Commission Radiofrequency Exposure Limits and Policies; Date: Mar. 29, 2013 (Year: 2013).*
(Continued)

*Primary Examiner* — Steven Lim
*Assistant Examiner* — Muhammad Adnan
(74) *Attorney, Agent, or Firm* — Andrew J. Hagerty; Richard L. Alexander

(57) ABSTRACT

A sensor system for detecting a property of or within an absorbent article. The system may comprise a first sensor and a first transmitter. The sensor may be disposed in or on the absorbent article. The sensor may have a first status and may be capable of changing to a second status. The first transmitter may be capable of sensing a change in status of the sensor from the first status to the second status. The first transmitter may be capable of checking the status of the sensor noncontinuously. The first transmitter may programmed to check the status of the first sensor at least every 5 minutes but not longer than every 2 hours.

28 Claims, 6 Drawing Sheets

Related U.S. Application Data

(60) Provisional application No. 61/863,595, filed on Aug. 8, 2013.

(51) Int. Cl.
*A61F 13/49* (2006.01)
*A61F 13/15* (2006.01)

(56) References Cited

U.S. PATENT DOCUMENTS

| | | | |
|---|---|---|---|
| 3,911,173 A | 10/1975 | Sprague, Jr. | |
| 4,022,210 A * | 5/1977 | Glassman | A61F 13/493 604/394 |
| 4,265,245 A * | 5/1981 | Glassman | A61F 13/493 604/365 |
| 4,286,331 A * | 8/1981 | Anderson | G08B 25/016 340/540 |
| 4,515,595 A | 5/1985 | Kievit et al. | |
| 4,554,662 A * | 11/1985 | Suzuki | G03G 15/55 714/44 |
| 4,573,986 A | 3/1986 | Minetola et al. | |
| 4,662,875 A | 5/1987 | Hirotsu et al. | |
| 4,681,793 A | 7/1987 | Linman et al. | |
| 4,695,278 A | 9/1987 | Lawson | |
| 4,699,622 A | 10/1987 | Toussant et al. | |
| 4,710,189 A | 12/1987 | Lash | |
| 4,785,996 A | 11/1988 | Ziecker et al. | |
| 4,795,454 A | 1/1989 | Dragoo | |
| 4,808,178 A | 2/1989 | Aziz | |
| 4,842,666 A | 6/1989 | Werenicz | |
| 4,846,815 A | 7/1989 | Molloy | |
| 4,894,060 A | 1/1990 | Nestegard | |
| 4,909,803 A | 3/1990 | Aziz et al. | |
| 4,940,464 A | 7/1990 | Van Gompel et al. | |
| 4,946,527 A | 8/1990 | Battrell | |
| 4,963,140 A | 10/1990 | Robertson et al. | |
| 5,137,537 A | 8/1992 | Herron et al. | |
| 5,151,092 A | 9/1992 | Buell et al. | |
| 5,221,274 A | 6/1993 | Buell et al. | |
| 5,242,436 A | 9/1993 | Weil et al. | |
| 5,264,830 A | 11/1993 | Kline et al. | |
| 5,354,289 A | 10/1994 | Mitchell et al. | |
| 5,433,715 A | 7/1995 | Tanzer et al. | |
| 5,469,145 A | 11/1995 | Johnson | |
| 5,499,978 A | 3/1996 | Buell et al. | |
| 5,507,736 A | 4/1996 | Clear et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,591,152 A | 1/1997 | Buell et al. | |
| 5,607,414 A | 3/1997 | Richards et al. | |
| 5,700,254 A | 12/1997 | McDowall et al. | |
| 5,709,222 A | 1/1998 | Davallou | |
| 5,714,156 A | 2/1998 | Schmidt et al. | |
| 5,838,240 A | 11/1998 | Johnson | |
| 5,865,823 A | 2/1999 | Curro | |
| 5,902,222 A | 5/1999 | Wessman | |
| 5,938,648 A | 8/1999 | LaVon et al. | |
| 5,959,535 A | 9/1999 | Remsburg | |
| 6,004,306 A | 12/1999 | Robles et al. | |
| 6,160,198 A | 3/2000 | Roe et al. | |
| 6,066,774 A * | 5/2000 | Roe | A61F 13/42 604/358 |
| 6,093,869 A | 7/2000 | Roe et al. | |
| 6,121,509 A | 9/2000 | Ashraf et al. | |
| 6,203,496 B1 | 3/2001 | Gael et al. | |
| 6,359,190 B1 * | 3/2002 | Ter-Ovanesyan | A61B 5/04884 128/886 |
| 6,372,951 B1 | 4/2002 | Ovanesyan et al. | |
| 6,384,296 B1 | 5/2002 | Roe et al. | |
| 6,432,098 B1 | 8/2002 | Kline et al. | |
| 6,501,002 B1 | 12/2002 | Roe et al. | |
| 6,534,149 B1 | 3/2003 | Daley et al. | |
| 6,603,403 B2 | 8/2003 | Jeutter et al. | |
| 6,609,068 B2 * | 8/2003 | Cranley | A61B 5/00 702/24 |
| 6,617,488 B1 * | 9/2003 | Springer | A61F 13/42 604/360 |
| 6,632,504 B1 | 10/2003 | Gillespie et al. | |
| 6,645,190 B1 | 11/2003 | Olson et al. | |
| 6,645,569 B2 | 11/2003 | Cramer et al. | |
| 6,863,933 B2 | 3/2005 | Cramer et al. | |
| 6,946,585 B2 | 9/2005 | London Brown | |
| 6,975,230 B1 * | 12/2005 | Brilman | A61B 5/0002 340/572.8 |
| 7,002,054 B2 | 2/2006 | Allen et al. | |
| 7,049,969 B2 | 5/2006 | Tamai | |
| 7,112,621 B2 | 9/2006 | Rohrbaugh et al. | |
| 7,174,774 B2 * | 2/2007 | Pawar | A61F 13/42 434/365 |
| 7,241,627 B2 | 7/2007 | Wilhelm et al. | |
| 7,250,547 B1 | 7/2007 | Hofmeister et al. | |
| 7,295,125 B2 | 11/2007 | Gabriel | |
| 7,355,090 B2 | 4/2008 | Alex, III et al. | |
| 7,394,391 B2 | 7/2008 | Long | |
| 7,449,614 B2 | 11/2008 | Alex, III | |
| 7,477,156 B2 | 1/2009 | Long et al. | |
| 7,489,252 B2 | 2/2009 | Long et al. | |
| 7,498,478 B2 | 3/2009 | Long et al. | |
| 7,504,550 B2 | 3/2009 | Tippey et al. | |
| 7,524,195 B2 | 4/2009 | Ales et al. | |
| 7,537,832 B2 | 5/2009 | Carlucci et al. | |
| 7,595,734 B2 | 9/2009 | Long et al. | |
| 7,642,396 B2 | 1/2010 | Alex, III et al. | |
| 7,649,125 B2 | 1/2010 | Ales, III et al. | |
| 7,659,815 B2 | 2/2010 | Cohen et al. | |
| 7,667,806 B2 | 2/2010 | Ales et al. | |
| 7,700,820 B2 | 4/2010 | Tippey et al. | |
| 7,700,821 B2 | 4/2010 | Ales, III et al. | |
| 7,737,322 B2 | 6/2010 | Alex, III et al. | |
| 7,753,691 B2 | 7/2010 | Ales et al. | |
| 7,760,101 B2 | 7/2010 | Ales, III et al. | |
| 7,786,341 B2 | 8/2010 | Schneider et al. | |
| 7,789,869 B2 | 9/2010 | Berland et al. | |
| 7,803,319 B2 | 9/2010 | Yang et al. | |
| 7,812,731 B2 | 10/2010 | Bunza et al. | |
| 7,834,235 B2 | 11/2010 | Long et al. | |
| 7,835,925 B2 | 11/2010 | Roe et al. | |
| 7,846,383 B2 | 12/2010 | Song | |
| 7,850,470 B2 | 12/2010 | Ales et al. | |
| 7,855,653 B2 | 12/2010 | Rondoni et al. | |
| 7,879,392 B2 | 2/2011 | Wenzel et al. | |
| 7,956,754 B2 | 4/2011 | Long | |
| 7,946,869 B2 | 5/2011 | Ales et al. | |
| 7,973,210 B2 | 7/2011 | Long et al. | |
| 8,044,258 B2 * | 10/2011 | Hietpas | A61F 13/42 604/361 |
| 8,053,625 B2 | 11/2011 | Nhan et al. | |
| 8,057,454 B2 | 11/2011 | Long et al. | |
| 8,058,194 B2 | 11/2011 | Nhan et al. | |
| 8,101,813 B2 | 1/2012 | Ales et al. | |
| 8,111,165 B2 | 2/2012 | Ortega et al. | |
| 8,115,643 B2 | 2/2012 | Wada et al. | |
| 8,172,982 B2 | 5/2012 | Ales et al. | |
| 8,173,380 B2 | 5/2012 | Yang et al. | |
| 8,183,876 B2 | 5/2012 | Wada et al. | |
| 8,196,270 B2 | 6/2012 | Mandzsu | |
| 8,196,809 B2 | 6/2012 | Thorstensson | |
| 8,207,394 B2 | 6/2012 | Feldkamp et al. | |
| 8,215,973 B2 | 7/2012 | Ales et al. | |
| 8,222,476 B2 | 7/2012 | Song et al. | |
| 8,237,572 B2 | 8/2012 | Clement et al. | |
| 8,248,249 B2 | 8/2012 | Clement et al. | |
| 8,264,362 B2 | 9/2012 | Ales et al. | |
| 8,274,393 B2 | 9/2012 | Ales et al. | |
| 8,299,317 B2 | 10/2012 | Tippey et al. | |
| 8,304,598 B2 | 11/2012 | Masbacher et al. | |
| 8,314,284 B1 * | 11/2012 | Novello | A61F 13/505 604/361 |
| 8,334,226 B2 | 12/2012 | Nhan et al. | |
| 8,334,425 B2 | 12/2012 | Ales et al. | |

(56) References Cited

U.S. PATENT DOCUMENTS

| | | | |
|---|---|---|---|
| 8,338,659 B2 | 12/2012 | Collins et al. | |
| 8,350,694 B1* | 1/2013 | Trundle | G08B 25/08 |
| | | | 340/539.11 |
| 8,372,242 B2 | 2/2013 | Ales et al. | |
| 8,372,766 B2 | 2/2013 | Nhan et al. | |
| 8,378,167 B2 | 2/2013 | Allen et al. | |
| 8,381,536 B2 | 2/2013 | Nhan et al. | |
| 8,384,378 B2 | 2/2013 | Feldkamp et al. | |
| 8,395,014 B2 | 3/2013 | Helmer et al. | |
| 8,416,088 B2 | 4/2013 | Ortega et al. | |
| 8,431,766 B1 | 4/2013 | Lonero | |
| 8,440,877 B2 | 5/2013 | Collins et al. | |
| 8,452,388 B2 | 5/2013 | Feldkamp et al. | |
| 8,471,715 B2 | 6/2013 | Solazzo et al. | |
| 8,507,746 B2 | 8/2013 | Ong et al. | |
| 8,546,639 B2 | 10/2013 | Wada et al. | |
| 8,563,801 B2 | 10/2013 | Berland et al. | |
| 8,570,175 B2 | 10/2013 | Rahimi | |
| 8,604,268 B2 | 12/2013 | Cohen et al. | |
| 8,623,292 B2 | 1/2014 | Song et al. | |
| 8,628,506 B2 | 1/2014 | Ales, III et al. | |
| 8,882,731 B2 | 1/2014 | Suzuki et al. | |
| 8,642,832 B2 | 2/2014 | Ales et al. | |
| 8,697,933 B2 | 4/2014 | Ales, III et al. | |
| 8,697,934 B2 | 4/2014 | Nhan et al. | |
| 8,697,935 B2 | 4/2014 | Daanen | |
| 8,698,641 B2 | 4/2014 | Abraham et al. | |
| 8,742,198 B2 | 6/2014 | Wei et al. | |
| 8,773,117 B2 | 7/2014 | Feldkamp et al. | |
| 8,779,785 B2 | 7/2014 | Wada et al. | |
| 8,785,716 B2 | 7/2014 | Schaefer et al. | |
| 8,816,149 B2 | 8/2014 | Richardson et al. | |
| 8,866,052 B2 | 10/2014 | Nhan et al. | |
| 8,866,624 B2 | 10/2014 | Ales et al. | |
| 8,884,769 B2 | 11/2014 | Novak | |
| 8,889,944 B2 | 11/2014 | Abraham et al. | |
| 8,920,731 B2 | 12/2014 | Nhan et al. | |
| 8,933,291 B2 | 1/2015 | Wei et al. | |
| 8,933,292 B2 | 1/2015 | Abraham et al. | |
| 8,962,909 B2 | 2/2015 | Groosman et al. | |
| 8,975,465 B2 | 3/2015 | Hong et al. | |
| 8,978,452 B2 | 3/2015 | Johnson et al. | |
| 8,988,231 B2 | 3/2015 | Chen | |
| 9,018,434 B2* | 4/2015 | Ruman | A61F 13/42 |
| | | | 604/361 |
| 9,034,593 B2 | 5/2015 | Martin et al. | |
| 9,070,060 B2 | 6/2015 | Forster | |
| 9,072,634 B2 | 7/2015 | Hundorf et al. | |
| 9,131,893 B2* | 9/2015 | Faybishenko | G16H 50/20 |
| 9,211,218 B2 | 12/2015 | Rinnert et al. | |
| 9,295,593 B2 | 3/2016 | Van Malderen | |
| 9,380,977 B2 | 7/2016 | Abir | |
| 2002/0021220 A1 | 2/2002 | Dreyer | |
| 2002/0070864 A1 | 6/2002 | Jeutter et al. | |
| 2003/0105190 A1 | 6/2003 | Diehl et al. | |
| 2003/0148684 A1 | 8/2003 | Cramer et al. | |
| 2003/0208133 A1* | 11/2003 | Mault | A61B 5/0002 |
| | | | 600/532 |
| 2004/0064114 A1* | 4/2004 | David | A61F 13/42 |
| | | | 604/361 |
| 2004/0106202 A1 | 6/2004 | Zainiev et al. | |
| 2004/0127867 A1 | 7/2004 | Odorzynski et al. | |
| 2004/0220538 A1* | 11/2004 | Panopoulos | A61F 13/42 |
| | | | 604/361 |
| 2004/0236302 A1* | 11/2004 | Wilhelm | A61F 13/42 |
| | | | 604/389 |
| 2004/0254549 A1 | 12/2004 | Olson et al. | |
| 2005/0008839 A1 | 1/2005 | Cramer et al. | |
| 2005/0033250 A1* | 2/2005 | Collette | A61F 13/42 |
| | | | 604/361 |
| 2005/0065487 A1 | 3/2005 | Graef et al. | |
| 2005/0099294 A1* | 5/2005 | Bogner | A61B 5/0002 |
| | | | 340/540 |
| 2005/0124947 A1 | 6/2005 | Fernfors | |
| 2005/0137542 A1 | 6/2005 | Underhill et al. | |
| 2005/0195085 A1 | 9/2005 | Cretu-Petra | |
| 2006/0061477 A1* | 3/2006 | Yeh | A61F 13/42 |
| | | | 340/573.5 |
| 2006/0069362 A1* | 3/2006 | Odorzynski | A61F 13/42 |
| | | | 604/361 |
| 2006/0195068 A1* | 8/2006 | Lawando | A61F 13/42 |
| | | | 604/361 |
| 2006/0222675 A1 | 10/2006 | Sabnis et al. | |
| 2006/0264861 A1* | 11/2006 | LaVon | A61F 13/49413 |
| | | | 604/385.201 |
| 2007/0044805 A1* | 3/2007 | Wedler | A61M 16/024 |
| | | | 128/207.14 |
| 2007/0055210 A1 | 3/2007 | Kao | |
| 2007/0100666 A1* | 5/2007 | Stivoric | F24F 11/30 |
| | | | 705/3 |
| 2007/0142797 A1 | 6/2007 | Long et al. | |
| 2007/0151885 A1* | 7/2007 | Loyd | A61F 13/55185 |
| | | | 206/440 |
| 2007/0156106 A1* | 7/2007 | Klofta | A61F 13/42 |
| | | | 604/361 |
| 2007/0185467 A1 | 8/2007 | Klofta et al. | |
| 2007/0233027 A1 | 10/2007 | Roe et al. | |
| 2007/0252710 A1* | 11/2007 | Long | A61F 13/42 |
| | | | 340/573.5 |
| 2007/0252713 A1 | 11/2007 | Rondoni et al. | |
| 2007/0255241 A1 | 11/2007 | Weber et al. | |
| 2007/0255242 A1 | 11/2007 | Ales, III et al. | |
| 2007/0270774 A1 | 11/2007 | Bergman et al. | |
| 2008/0001735 A1* | 1/2008 | Tran | G06F 19/3418 |
| | | | 340/539.22 |
| 2008/0021423 A1* | 1/2008 | Klofta | A61F 13/15 |
| | | | 604/361 |
| 2008/0021428 A1 | 1/2008 | Klofta et al. | |
| 2008/0052030 A1 | 2/2008 | Olson et al. | |
| 2008/0054408 A1 | 3/2008 | Tippey et al. | |
| 2008/0057693 A1 | 3/2008 | Tippey et al. | |
| 2008/0058740 A1 | 3/2008 | Sullivan et al. | |
| 2008/0058741 A1 | 3/2008 | Long et al. | |
| 2008/0082062 A1 | 4/2008 | Cohen et al. | |
| 2008/0082063 A1* | 4/2008 | Ales | A61F 13/42 |
| | | | 604/361 |
| 2008/0132859 A1 | 6/2008 | Pires | |
| 2008/0147031 A1 | 6/2008 | Long et al. | |
| 2008/0208155 A1* | 8/2008 | LaVon | A61F 13/49012 |
| | | | 604/385.3 |
| 2008/0234644 A1 | 9/2008 | Hansson et al. | |
| 2008/0266117 A1 | 10/2008 | Song et al. | |
| 2008/0266122 A1 | 10/2008 | Ales et al. | |
| 2008/0266123 A1* | 10/2008 | Ales | A61F 13/42 |
| | | | 340/604 |
| 2008/0269707 A1 | 10/2008 | Song | |
| 2008/0300559 A1* | 12/2008 | Gustafson | A61F 13/42 |
| | | | 604/361 |
| 2008/0312622 A1 | 12/2008 | Hundorf et al. | |
| 2009/0058072 A1 | 3/2009 | Weber et al. | |
| 2009/0062756 A1 | 3/2009 | Long et al. | |
| 2009/0124990 A1 | 5/2009 | Feldkamp et al. | |
| 2009/0155753 A1 | 6/2009 | Ales et al. | |
| 2009/0326409 A1 | 12/2009 | Cohen et al. | |
| 2010/0013778 A1* | 1/2010 | Liu | G06F 1/1626 |
| | | | 345/173 |
| 2010/0030173 A1 | 2/2010 | Song et al. | |
| 2010/0145294 A1 | 6/2010 | Song et al. | |
| 2010/0152688 A1 | 6/2010 | Handwerker et al. | |
| 2010/0159599 A1 | 6/2010 | Song et al. | |
| 2010/0159611 A1 | 6/2010 | Song et al. | |
| 2010/0160882 A1 | 6/2010 | Lowe | |
| 2010/0164733 A1* | 7/2010 | Ales | A61F 13/42 |
| | | | 340/604 |
| 2010/0168694 A1 | 7/2010 | Gakhar et al. | |
| 2010/0168702 A1 | 7/2010 | Ales et al. | |
| 2010/0241094 A1* | 9/2010 | Sherron | A61F 13/42 |
| | | | 604/361 |
| 2010/0277324 A1* | 11/2010 | Yeh | A61F 13/42 |
| | | | 340/573.5 |

(56) References Cited

U.S. PATENT DOCUMENTS

| | | | |
|---|---|---|---|
| 2011/0251038 A1* | 10/2011 | LaVon | A61F 13/15747 493/405 |
| 2011/0298597 A1* | 12/2011 | Kaihori | G08C 17/02 340/13.25 |
| 2012/0061016 A1* | 3/2012 | LaVon | A61F 13/15593 156/226 |
| 2012/0116337 A1* | 5/2012 | Ales | A61F 13/42 604/361 |
| 2012/0130330 A1 | 5/2012 | Wilson et al. | |
| 2012/0157947 A1 | 6/2012 | Nhan et al. | |
| 2012/0172824 A1* | 7/2012 | Khaknazarov | A61F 13/42 604/361 |
| 2012/0190956 A1* | 7/2012 | Connolly | A61B 5/0537 600/372 |
| 2012/0206265 A1* | 8/2012 | Solazzo | A61F 13/42 340/573.5 |
| 2012/0215190 A1 | 8/2012 | Kawashima | |
| 2012/0225200 A1 | 9/2012 | Mandzsu | |
| 2012/0245541 A1* | 9/2012 | Suzuki | A61F 5/441 604/319 |
| 2012/0245542 A1* | 9/2012 | Suzuki | A61F 5/451 604/319 |
| 2012/0253303 A1* | 10/2012 | Suzuki | A61F 5/451 604/319 |
| 2012/0256750 A1* | 10/2012 | Novak | A61F 13/42 340/573.5 |
| 2012/0282681 A1 | 11/2012 | Teixeira et al. | |
| 2012/0299721 A1* | 11/2012 | Jones | B60R 25/33 340/521 |
| 2012/0310190 A1 | 12/2012 | LaVon et al. | |
| 2012/0310192 A1 | 12/2012 | Suzuki et al. | |
| 2012/0323194 A1 | 12/2012 | Suzuki et al. | |
| 2013/0012896 A1 | 1/2013 | Suzuki et al. | |
| 2013/0018340 A1 | 1/2013 | Abraham et al. | |
| 2013/0023786 A1 | 1/2013 | Mani et al. | |
| 2013/0041334 A1* | 2/2013 | Prioleau | A61F 13/42 604/361 |
| 2013/0076509 A1 | 3/2013 | Ahn | |
| 2013/0110061 A1 | 5/2013 | Abraham et al. | |
| 2013/0110063 A1* | 5/2013 | Abraham | A61F 13/42 604/361 |
| 2013/0131618 A1 | 5/2013 | Abraham et al. | |
| 2013/0151186 A1 | 6/2013 | Feldkamp | |
| 2013/0161380 A1 | 6/2013 | Joyce et al. | |
| 2013/0162402 A1 | 6/2013 | Amann et al. | |
| 2013/0162403 A1 | 6/2013 | Stiemer et al. | |
| 2013/0162404 A1 | 6/2013 | Stiemer et al. | |
| 2013/0165809 A1 | 6/2013 | Abir | |
| 2013/0261409 A1* | 10/2013 | Pathak | A61B 5/0022 600/301 |
| 2013/0303867 A1 | 11/2013 | Elfström et al. | |
| 2013/0307570 A1 | 11/2013 | Bosaeus et al. | |
| 2013/0321007 A1 | 12/2013 | Elfström et al. | |
| 2013/0324955 A1 | 12/2013 | Wong et al. | |
| 2014/0014716 A1 | 1/2014 | Joyce et al. | |
| 2014/0015644 A1 | 1/2014 | Amann et al. | |
| 2014/0015645 A1 | 1/2014 | Stiemer et al. | |
| 2014/0022058 A1 | 1/2014 | Stiemer et al. | |
| 2014/0062663 A1 | 3/2014 | Bourilkov et al. | |
| 2014/0121487 A1 | 5/2014 | Faybishenko et al. | |
| 2014/0152442 A1 | 6/2014 | Li | |
| 2014/0155850 A1 | 6/2014 | Shah et al. | |
| 2014/0155851 A1 | 6/2014 | Ales et al. | |
| 2014/0163502 A1 | 6/2014 | Arzti et al. | |
| 2014/0188063 A1 | 7/2014 | Nhan et al. | |
| 2014/0198203 A1* | 7/2014 | Vardi | G08B 21/20 348/135 |
| 2014/0200538 A1 | 7/2014 | Euliano et al. | |
| 2014/0241954 A1 | 8/2014 | Phillips et al. | |
| 2014/0242613 A1 | 8/2014 | Takeuchi et al. | |
| 2014/0242715 A1 | 8/2014 | Nhan et al. | |
| 2014/0266736 A1* | 9/2014 | Cretu-Petra | A61F 13/42 340/573.5 |
| 2014/0329212 A1 | 11/2014 | Ruman et al. | |
| 2014/0329213 A1 | 11/2014 | Ruman et al. | |
| 2014/0363354 A1 | 12/2014 | Phillips et al. | |
| 2015/0025347 A1 | 1/2015 | Song | |
| 2015/0042489 A1 | 2/2015 | LaVon | |
| 2015/0112202 A1* | 4/2015 | Abir | A61B 5/7455 600/473 |
| 2015/0130637 A1 | 5/2015 | Sengstaken, Jr. | |
| 2015/0150732 A1 | 6/2015 | Abir | |
| 2015/0157512 A1 | 6/2015 | Abir | |
| 2015/0317684 A1 | 11/2015 | Abir | |
| 2017/0156594 A1* | 6/2017 | Stivoric | A61B 5/7275 |

FOREIGN PATENT DOCUMENTS

| | | |
|---|---|---|
| EP | 1 216 673 B1 | 10/2005 |
| EP | 1 542 635 B1 | 4/2012 |
| EP | 2679209 | 1/2014 |
| EP | 2740450 | 6/2014 |
| EP | 2 491 899 B1 | 7/2014 |
| JP | 2002/022687 A | 1/2002 |
| JP | 2002/143199 A | 5/2002 |
| JP | 2003/190209 A | 7/2003 |
| JP | 2004/230135 A | 8/2004 |
| JP | 2006/296566 A | 11/2006 |
| WO | WO 95/10996 | 4/1995 |
| WO | WO 95/11652 | 5/1995 |
| WO | WO 95/016746 | 6/1995 |
| WO | WO 99/034841 | 7/1999 |
| WO | WO 99/34842 | 7/1999 |
| WO | WO 2000/59430 | 10/2000 |
| WO | WO 02/064877 | 8/2002 |
| WO | WO 02/067809 | 9/2002 |
| WO | WO 2007/122524 | 11/2007 |
| WO | WO 2008/155699 | 12/2008 |
| WO | WO 2010/123364 A1 | 10/2010 |
| WO | WO 2010/123425 A1 | 10/2010 |
| WO | WO 2011/013874 A1 | 2/2011 |
| WO | WO 2012/052172 | 4/2012 |
| WO | WO 2012/084925 A1 | 6/2012 |
| WO | WO 2012/126507 A1 | 9/2012 |
| WO | WO 2012/166765 | 12/2012 |
| WO | WO 2013/003905 A1 | 1/2013 |
| WO | WO 2013/016765 A1 | 2/2013 |
| WO | WO 2013/061963 A1 | 5/2013 |
| WO | WO 2013/091707 A1 | 6/2013 |
| WO | WO 2013/091728 A1 | 6/2013 |
| WO | WO 2013/095222 A1 | 6/2013 |
| WO | WO 2013/095226 A1 | 6/2013 |
| WO | WO 2013/095230 A1 | 6/2013 |
| WO | WO 2013/095231 A1 | 6/2013 |
| WO | WO 2013/097899 A1 | 7/2013 |
| WO | WO 2013/181436 A1 | 12/2013 |
| WO | WO 2013/185419 A1 | 12/2013 |
| WO | WO 2013/189284 A1 | 12/2013 |
| WO | WO 2014/035302 A1 | 3/2014 |
| WO | WO 2014/035340 A1 | 3/2014 |
| WO | WO 2014/122169 A1 | 8/2014 |
| WO | WO 2014/137671 A1 | 9/2014 |
| WO | WO 2014/146693 A1 | 9/2014 |
| WO | WO 2014/146694 A1 | 9/2014 |
| WO | WO 2014/148957 A1 | 9/2014 |
| WO | WO 2014/177200 A1 | 11/2014 |
| WO | WO 2014/177203 A1 | 11/2014 |
| WO | WO 2014/177204 A1 | 11/2014 |
| WO | WO 2014/177205 A1 | 11/2014 |
| WO | WO 2014/178763 A1 | 11/2014 |
| WO | WO 2014/192978 A1 | 12/2014 |
| WO | WO 2015/003712 A1 | 1/2015 |
| WO | WO 2015/068124 A1 | 5/2015 |
| WO | WO 2015/102084 A1 | 7/2015 |
| WO | WO 2015/102085 A1 | 7/2015 |

OTHER PUBLICATIONS

All Office Actions, U.S. Appl. No. 14/455,088.

(56) References Cited

OTHER PUBLICATIONS

International Search Report and Written Opinion, PCT/US2014/050083, dated Oct. 28, 2014.

* cited by examiner

SENSOR SYSTEMS FOR ABSORBENT ARTICLES COMPRISING SENSOR GATES

CROSS REFERENCE TO RELATED APPLICATIONS

This application is a continuation of, and claims priority under 35 U.S.C. § 120 to, U.S. patent application Ser. No. 14/455,088, filed on Aug. 8, 2014, which claims the benefit, under 35 USC § 119(e), of U.S. Provisional Patent Application Ser. No. 61/863,595 filed on Aug. 8, 2013, which is herein incorporated by reference in its entirety.

FIELD

In general, embodiments of the present disclosure relate to sensors for use with absorbent articles. In particular, embodiments of the present disclosure relate to sensor systems comprising a transmitter that utilizes one or more sensors to manage the amount of energy it emits.

BACKGROUND

The art discloses many different types of sensors that are integral with or attached to an absorbent article. These sensors are used to monitor wetness, temperature, etc. These sensors normally comprise a sensor component and a transmitting component. The transmitting component may send signals to a remote device, such as a cell phone or a remote, e.g. mobile, receiver, etc. One of the concerns with many of these designs is the amount of energy emitted by the transmitter, since many of these systems place the transmitter on or near the baby—and often around the genitals. Some transmitters emit energy constantly. In addition, some systems having sensors and a power source comprise sensors that are constantly under power. Many of the sensors are also placed in the genital area of the absorbent article and therefore emit some level of electrical energy in the genital area. From a functionality and power conservation standpoint, it is often not necessary to continually check for a change of state (e.g., within the absorbent article, such as an insult of urine and/or fecal matter). In fact, intermittent checks, for example 1 second out of 10 seconds, will provide a level of accuracy sufficient for many applications and will reduce exposure 10 fold. Some sensors may be able to detect a change in state with as little as a few milliseconds potentially reducing the exposure by more than 100 times potentially reducing the exposure by as much as 1000 times.

It is a goal to overcome the challenges mentioned above. Particularly, one object of the present disclosure is to create sensor systems having one or more sensors such that the sensor system can use low energy to check on the various sensors before initiating transmission of a stronger signal to a remote device. Further, it is an object of the present disclosure to avoid sending any signal to a second or third sensor if the first sensor is of a certain status. It is also an object of the present disclosure to use a single sensor with multiple leads that can collect information from multiple parts of the absorbent article. All of these objects help to minimize exposing the wearer of absorbent articles to energy emitted by the sensor system.

DETAILED DESCRIPTION

Figure 1A:
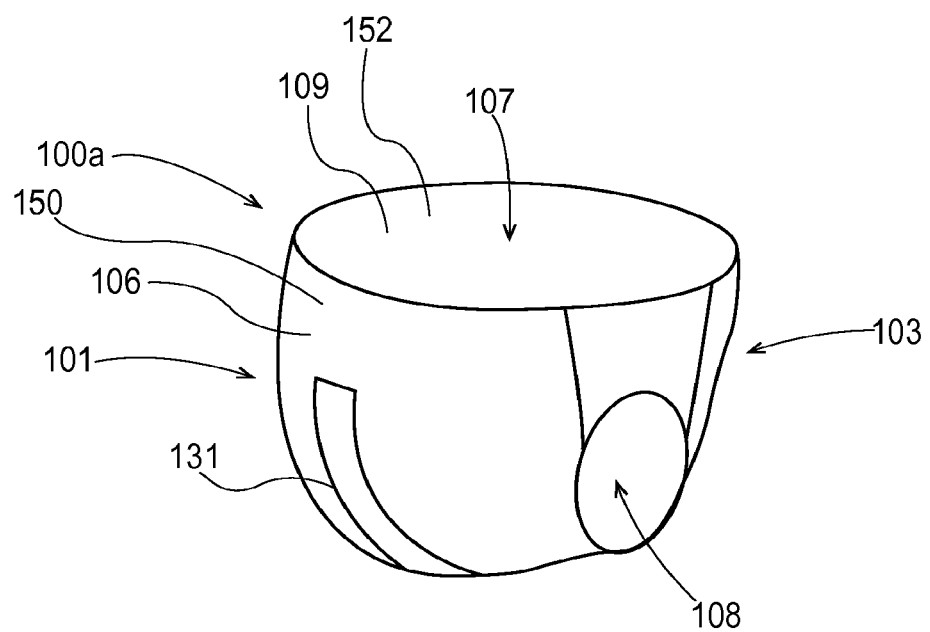
FIG. 1A illustrates a perspective view a pant-type absorbent article with a sensor in the front, according to embodiments of the present disclosure.

Sensors of the present disclosure may be used with various absorbent articles and/or auxiliary articles to make a sensor system.

Absorbent Article

The absorbent article may be one for personal wear, including but not limited to diapers, training pants, feminine hygiene products, incontinence products, medical garments, surgical pads and bandages, other personal care or health care garments, and the like. Various materials and methods for constructing absorbent articles such as diapers and pants are disclosed in U.S. application Ser. No. 12/914,494 (Publication No. 2011-0041999, filed on Oct. 28, 2010 (hereinafter, "the '494 App."), U.S. application Ser. No. 12/781,993 (Publication No. 2010-0228211, filed on May 18, 2010 (hereinafter, "the '993 App."), U.S. application Ser. No. 11/709,500 (Publication No. 2008-0208155, filed on Feb. 22, 2007 (hereinafter, "the '500 App."), and U.S. application Ser. No. 12/434,927 (Publication No. 2009-0312734, filed on May 4, 2009 (hereinafter, "the '927 App.").

The sensor may be discrete from or integral with the absorbent article. The absorbent article may comprise sensors that can sense various aspects of the absorbent article associated with insults of bodily exudates such as urine and/or BM (e.g., the sensor may sense variations in temperature, humidity, presence of ammonia or urea, various other vaporous components of the exudates (urine and feces), changes in moisture vapor transmission through the absorbent articles garment-facing layer, changes in translucence of the garment-facing layer, color changes through the garment-facing layer, etc.). Additionally, the sensors my sense components of urine, such as ammonia or urea and/or byproducts resulting from reactions of these components with the absorbent article. The sensor may sense byproducts that are produced when urine and/or BM contacts or mixes with other components of the absorbent article (e.g., adhesives, agm, etc.). The components or byproducts being sensed may be present as vapors that may pass through the garment-facing layer. It may also be desirable to place reactants in the diaper that change state (e.g. color, temperature, etc.) or create a measurable byproduct when mixed with urine and/or BM. The sensor may also sense changes in pH, pressure, mechanical (example—strain, stress, and/or failure), motion, light, odor, thickness, density, the presence of gas, blood, a chemical marker or a biological marker or combinations thereof.

One or more parts or portions of the sensor system may be removably integrated with the absorbent article and/or an auxiliary article (designed to fit over at least a portion of the absorbent article) with hook and loops fasteners, adhesives, thermal bonds, mating fasteners like snaps or buttons, or may be disposed in pockets, recesses or void spaces built into the absorbent article, or combinations thereof. Many of these integration means enable removal of and/or attachment of the sensor from or to the absorbent article. The absorbent article may further comprise graphics for the purpose of properly locating the sensor. In addition, in cases where an auxiliary article is present, the auxiliary article may be joined to the absorbent article by similar integration means.

FIG. 1A illustrates an outside perspective view of a front 101 and a side 103 of a pant-type absorbent article 100A formed for wearing. The pant-type absorbent article 100A may include a waist opening 107, a leg opening 108, an exterior surface (garment-facing) 106 formed by a garment-facing layer 150A sometimes referred to as the garment-facing surface, and an interior surface (wearer-facing) 109 formed by a wearer-facing layer 152A sometimes referred to as the wearer-facing surface. The absorbent article 100A may include a longitudinally oriented sensor 131 disposed in the front 101.

The wearer-facing layer 152A may be a layer of one or more materials that forms at least a portion of the inside of the front-fastenable wearable absorbent article and faces a wearer when the absorbent article 100A is worn by the wearer. In FIG. 1A, a portion of the wearer-facing layer 152A is illustrated as broken-away, in order to show the garment-facing layer 150A. A wearer-facing layer is sometimes referred to as a topsheet. The wearer-facing layer 152A is configured to be liquid permeable, such that bodily fluids received by the absorbent article 100A can pass through the wearer-facing layer 152A to the absorbent material 154A. In various embodiments, a wearer-facing layer can include a nonwoven material and/or other materials as long as the materials are liquid permeable over all or part of the wearer-facing layer.

The absorbent material 154A may be disposed subjacent to the wearer-facing layer 152A and superjacent to the garment-facing layer 150A, in at least a portion of the absorbent article 100A. In some embodiments, an absorbent material of an absorbent article is part of a structure referred to as an absorbent core. The absorbent material 154A may be configured to be liquid absorbent, such that the absorbent material 154A can absorb bodily fluids received by the absorbent article 100A. In various embodiments, an absorbent material can include cellulosic fibers (e.g., wood pulp fibers), other natural fibers, synthetic fibers, woven or non-woven sheets, scrim netting or other stabilizing structures, superabsorbent material, foams, binder materials, adhesives, surfactants, selected hydrophobic materials, pigments, lotions, odor control agents or the like, as well as combinations thereof. The absorbent structure may comprise one or more storage layers and one or more surge management layers. A pair of containment flaps, elasticated leg cuffs, may form a portion of the interior surface of the absorbent assembly for inhibiting the lateral flow of body exudates. One or more of the layers of the absorbent structure may comprise apertures or openings therein. One such embodiment would be one or more apertures or openings in the crotch region in the region of the absorbent article wherein BM is deposited. The opening will provide a more direct means of measurement by a sensor when BM is present or may provide a more direct means for the sensor to monitor the environment inside the article.

The garment-facing layer 150A may be a layer formed of one or more materials that form at least a portion of an outside of the wearable absorbent article and may face a wearer's garments when the absorbent article 100A is worn by the wearer. A garment-facing layer is sometimes referred to as a backsheet. The garment-facing layer 150A may be configured to be liquid impermeable, such that bodily fluids received by the absorbent article 100A cannot pass through the garment-facing layer 150A. In various embodiments, a garment-facing layer can include a nonporous film, a porous film, a woven material, a non-woven fibrous material or combinations thereof. The outer cover may also be stretchable, extensible, and in some embodiments it may be elastically extensible or elastomeric. The garment-facing layer 150A may also be vapor permeable and yet liquid impervious.

Throughout the present disclosure, a reference to a pant-type absorbent article can refer to an embodiment that is side-fastenable or to an embodiment without fasteners. A reference to a pant-type absorbent article refers to an article having preformed waist and/or leg openings. Thus, each embodiment of an absorbent article of the present disclosure that is described as pant-type can be configured in any of these ways, as will be understood by one of ordinary skill in the art.

Figure 1B:
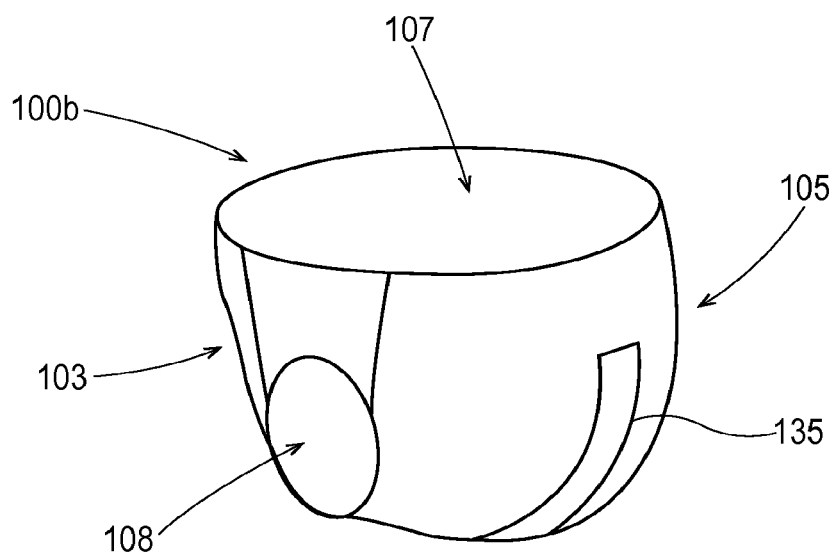
FIG. 1B illustrates a perspective view a pant-type absorbent article with a sensor in the back, according to embodiments of the present disclosure.

FIG. 1B illustrates an outside perspective view of a side 103 and a back 105 of a pant-type absorbent article 100B formed for wearing. The pant-type absorbent article 100B may include a waist opening 107 and a leg opening 108. Absorbent article 100B may include a longitudinally oriented sensor 135 in the back 105.

Figure 1C:
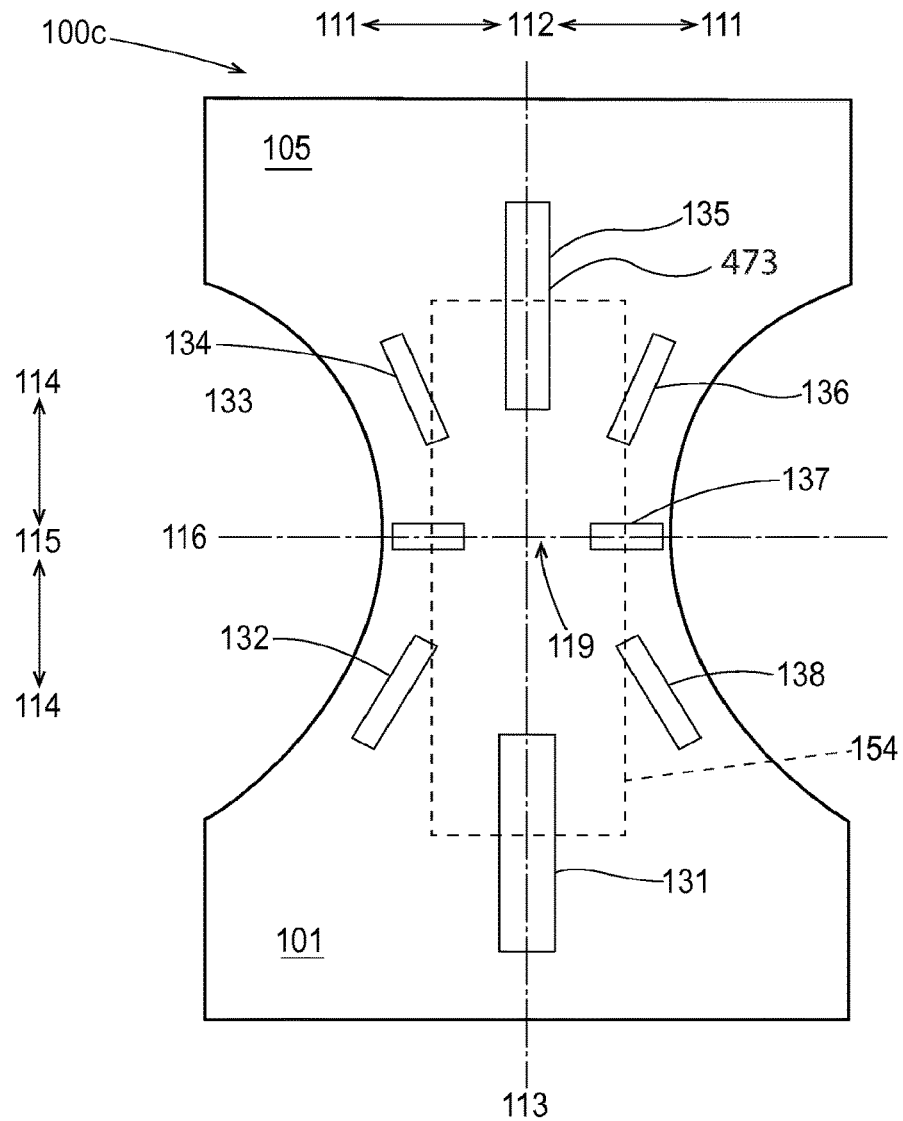
FIG. 1C illustrates a top plan view of the inner (wearer-facing) surface of a pant-type absorbent article opened and laid flat with a plurality of sensors, according to embodiments of the present disclosure.

FIG. 1C illustrates an outside plan view of a pant-type absorbent article 100C laid out flat. The absorbent article 100C may include a front 101 and a back 105, separated by a lateral centerline 116.

In FIG. 1C, a longitudinal centerline 113 and the lateral centerline 116 provide lines of reference for referring to relative locations of the absorbent article 100C. When a first location 112 is nearer to the longitudinal centerline 113 than a second location 111, the first location 112 can be considered laterally inboard to the second location 111. Similarly, the second location 111 can be considered laterally outboard from the first location 112. When a third location 115 is nearer to the lateral centerline 116 than a fourth location 114, the third location 115 can be considered longitudinally inboard to the fourth location 114. Also, the fourth location 114 can be considered longitudinally outboard from the third location 115.

A reference to an inboard location, without a lateral or longitudinal limitation, refers to a location of the absorbent article 100C that is laterally inboard and/or longitudinally inboard to another location. In the same way, a reference to an outboard location, without a lateral or longitudinal limitation, refers to a location of the absorbent article 100C that is laterally outboard and/or longitudinally outboard from another location.

Inboard and outboard can also be understood with reference to a center of an absorbent article. The longitudinal centerline 113 and the lateral centerline 116 cross at a center 119 of the absorbent article 100C. When one location is nearer to the center 119 than another location, the one location can be considered inboard to the other location. The one location can be inboard laterally, or longitudinally, or both laterally and longitudinally. The other location can be considered outboard from the one location. The other location can be outboard laterally, or longitudinally, or both laterally and longitudinally.

FIG. 1C includes arrows indicating relative directions for laterally outboard 111 relative to 112, laterally inboard 112 relative to 111, longitudinally outboard 114 relative to 115, and longitudinally inboard 115 relative to 114, each with respect to the absorbent article 100C. Throughout the present disclosure, a reference to a longitudinal dimension, measurement, line, or direction refers to a dimension, measurement, line, or direction that is substantially or completely parallel to the longitudinal centerline 113 and a reference to a lateral dimension, measurement, line, or direction refers to a dimension, measurement, line, or direction that is substantially or completely parallel to the lateral centerline 116. The terminology for describing relative locations, as discussed above, is used for absorbent articles throughout the present disclosure. This terminology can also be similarly applied to various other absorbent articles, as will be understood by one of ordinary skill in the art.

The absorbent article 100C may include a number of sensors in various exemplary locations and orientations. The absorbent article 100C may include a longitudinally oriented sensor such as sensor 131 and 135, along the longitudinal centerline 113 in the front 101 and/or back 105. The front 101 and/or back 105 may include at least one angled sensor such as sensors 132, 134, 136 and 138 oriented at an angle between the longitudinal centerline 113 and the lateral centerline 116. The absorbent article 100C may include one or more laterally oriented sensors such as sensors 133 and 137 along the lateral centerline 116.

In the absorbent article 100C, the sensors may be oriented substantially radially out from the center 119. However, in addition to the locations and orientations illustrated in FIG. 1C, a sensor of the present disclosure can be disposed in various alternate locations and orientations relative to an absorbent article. As an example, a sensor can be disposed in a pant-type absorbent article at a location relative to a pee point for a wearer of the absorbent article.

Figure 4:
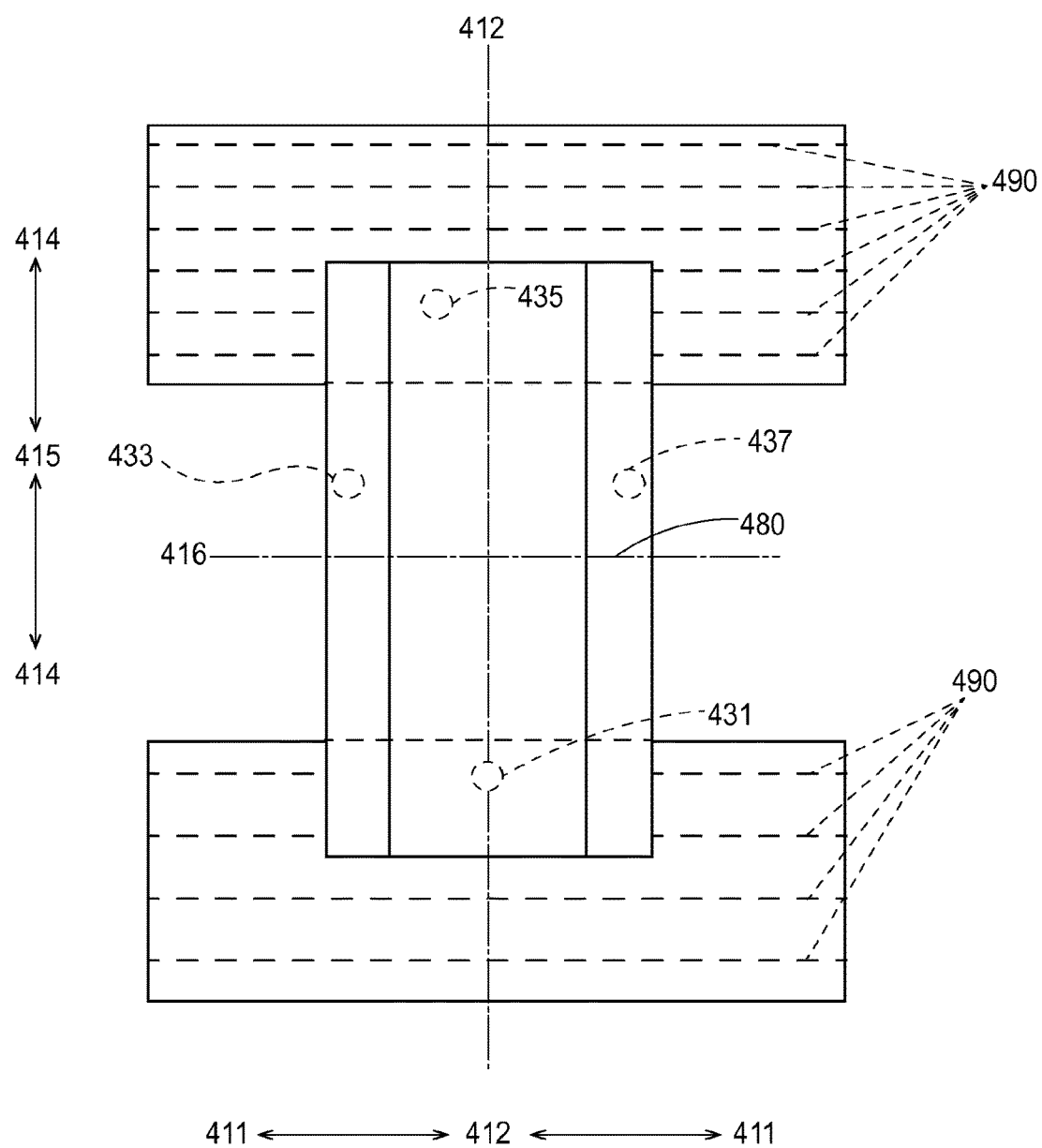
FIG. 4 illustrates a top plan view of the inner (wearer-facing) surface of a pant-type absorbent article opened and laid flat with sensors disposed at different locations, including the front, back, and cuffs, according to embodiments of the present disclosure.

The absorbent article or an auxiliary article of the present disclosure may comprise (1) materials, (2) construction (e.g., may comprise pockets, be in taped or pant form), as described by U.S. application Ser. No. 13/483,456 (Publication No. 2012-0310190), filed on May 30, 2012 (hereinafter, "the '456 App.") and U.S. application Ser. No. 13/483,463 (Publication No. 2012-0310191), filed on May 30, 2012 (hereinafter, "the '463 App.) and may be refastenable as described by U.S. application Ser. No. 13/010,040 (Publication No. US 2011-0178485), filed on Jan. 20, 2011 (hereinafter, "the '040 App."), U.S. application Ser. No. 13/010,052 (Publication No. US 2011-0173796), filed on Jan. 20, 2011 (hereinafter, "the '052 App."), U.S. application Ser. No. 13/010,062 (Publication No. US 2011-0178486), filed on Jan. 20, 2011 (hereinafter, "the '062 App."), U.S. application Ser. No. 13/010,072 (Publication No. US 2011-0174432), filed on Jan. 20, 2011 (hereinafter, "the '072 App."), and U.S. application Ser. No. 13/010,083 (Publication No.—US 2011-0178490), filed on Jan. 20, 2011 (hereinafter, "the '083 App."). As shown in FIG. 4, the absorbent article or an auxiliary article of the present disclosure may also comprise multiple strands (see FIG. 4, 490) between layers of the front and back regions, and as disclosed in U.S. Application No. 61/804,271, filed on Mar. 22, 2013 (hereinafter, "the '271 App.") and U.S. Application No. 61/804,276, filed on Mar. 22, 2013 (hereinafter, "the '276 App.") (US docket Nos. 12819 and 12820).

Figure 3:
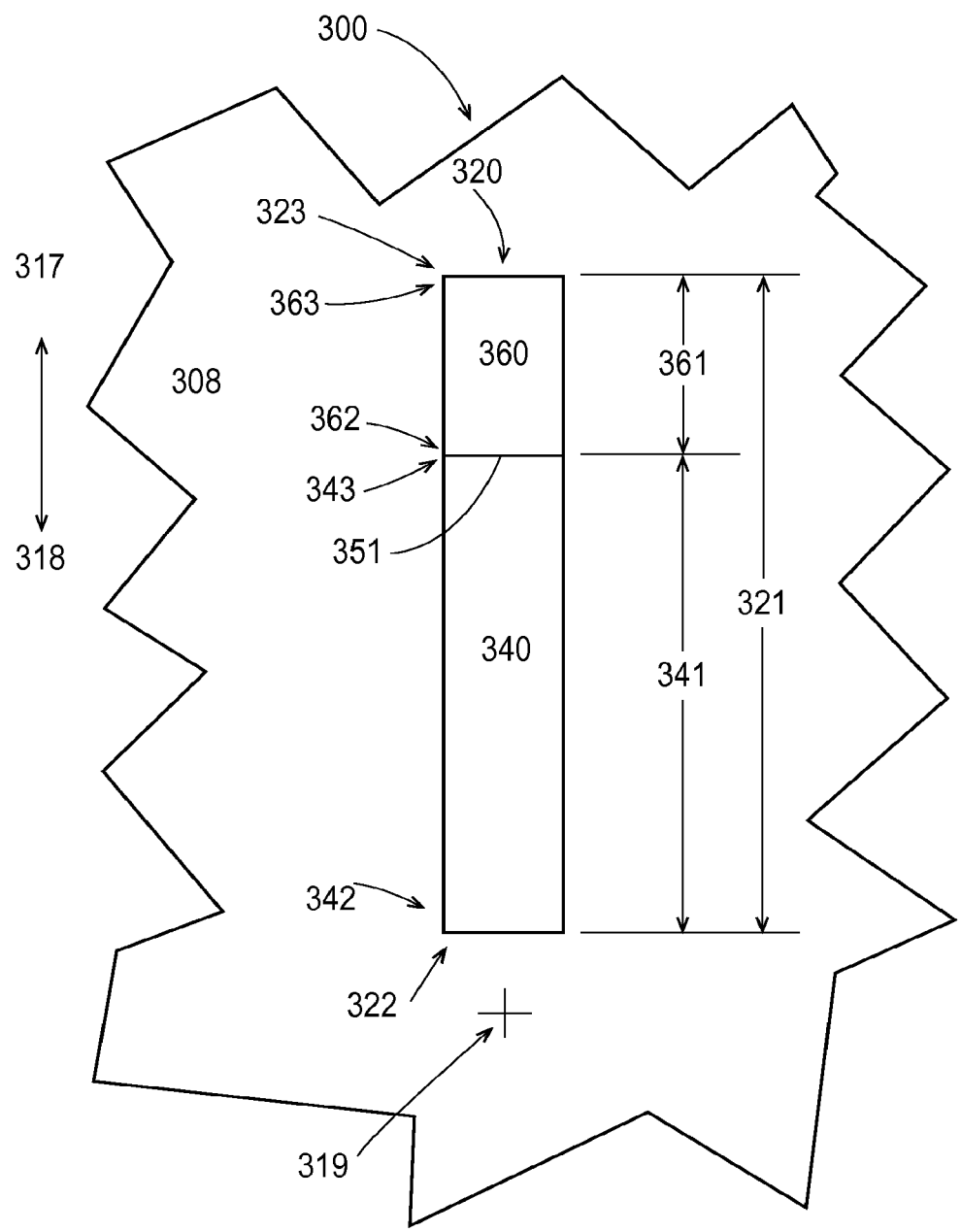
FIG. 3 illustrates a portion of an absorbent article with a sensor having a first sensing area and a second sensing area, according to embodiments of the present disclosure.

FIG. 3 illustrates an outside plan view of a portion 308 of an absorbent article 300 laid out flat. In various embodiments, the absorbent article 300 can be an absorbent article, such as a pant-type absorbent article or a fastenable absorbent article. In FIG. 3, outside edges of the portion 308 are broken lines, since the portion 308 is illustrated as separate from the rest of the absorbent article 300. For reference, FIG. 3 illustrates a center 319 of the absorbent article 300 and arrows indicating relative directions for outboard 317 and inboard 318 for the absorbent article 300.

The portion 308 of the absorbent article 300 may include a sensor 320. The sensor 320 may be disposed offset from the center 319. In various embodiments, one or more parts of a sensor can be disposed near, at, or overlapping a center of an absorbent article. For example, a single sensing area can extend from a front of an absorbent article, through the center of the absorbent article, to the back of the absorbent article. In such an embodiment, a farthest inboard point along the sensing area can be considered an inboard end of two sensors.

The sensor 320 may include an inboard end 322 and an outboard end 323. The sensor 320 has an overall sensor length 321, measured along the sensor 320 from the inboard end 322 to the outboard end 323. The sensor 320 may have an overall shape that is substantially elongated and substantially rectangular. The sensor 320 may have a substantially uniform width along the entire overall sensor length 321. It may be desirable that the sensor, or a portion of the sensor, has a bending stiffness of less than about 1000 N/m, 600 N/m, or 400 N/m (as determined by ASTM D 790-03) to keep it from irritating the wearer. It may alternatively or additionally be desirable to design the sensor, or a portion of the sensor, to have a bending modulus (N/m2) of less than 2.0E+09, 1.0E+08, or 1.0E+06.

In various embodiments a sensor can have an overall shape that is more or less elongated. In some embodiments, all or part of a sensor may be linear, curved, angled, segmented, or any regular or irregular geometric shape (such as a circle, square, rectangle, triangle, trapezoid, octagon, hexagon, star, half circle, a quarter circle, a half oval, a quarter oval, a radial pattern, etc.), a recognizable image (such as a letter, number, word, character, face of an animal, face of a person, etc.), or another recognizable image (such as a plant, a car, etc.), another shape, or combinations of any of these shapes. Also, in various embodiments, an indicator can have varying widths over all or part of its length.

The sensor 320 may include one or more sensing areas for example, a first sensing area 340 and a second sensing area 360. In various embodiments, a sensor can include three or more sensing areas.

The first sensing area 340 may include a first area inboard end 342, a first area outboard end 343, and a first area overall length 341 measured along the first sensing area 340 from the first area inboard end 342 to the first area outboard end 343. The first sensing area 340 may have an overall shape that is substantially elongated and substantially rectangular. The first sensing area 340 may have a substantially uniform width along the entire first area overall length 341. However, in some embodiments, a sensing area can have various shapes and various widths over all or part of its length, as described above in connection with the sensor.

In addition to the first sensing area 340, the sensor 320 may include a second sensing area 360. In the embodiment of FIG. 3, the second sensing area 360 is outboard 317 from the first sensing area 340. The second sensing area 360 may include a second area inboard end 362, a second area outboard end 363, and a second area overall length 361 measured along the second sensing area 360 from the second area inboard end 362 to the second area outboard end 363. In the embodiment of FIG. 3, the second area overall length 361 is less than the first area overall length 341. In some embodiments, a second area overall length can be equal to a first area overall length or greater than a first area overall length.

The second sensing area 360 may have an overall shape that is substantially elongated and substantially rectangular. The second sensing area 360 may have a substantially uniform width along the entire second area overall length 361.

Sensor Structure

As used in this application, the term "sensor" (e.g., 435) refers not only to the elements (e.g., 470, 471, and 472) responsible for detecting a stimulus and/or change in status of the article and signaling such detection (via impulse), but also may include the housing or carrier layer or substrate (e.g., 473) around such element(s). A "sensor" may include a carrier layer (e.g., 473) with multiple elements (e.g., 470, 471, and 472) capable of detecting one or more stimuli; and, the multiple elements may create multiple locations capable of detecting one or more stimuli. The sensors of the present disclosure may form a part of a sensor system capable of monitoring urine and/or fecal insults. The system may take on a variety of configurations, which are determined by the means in which the presence of urine and/or feces is detected. After detection of urine and/or feces, the system may inform a caregiver and/or a child by generating a notification. The notification may be and auditory signal, an olfactory signal, a tactile signal or a visual signal. It is understood that the system may comprise a device for sending a wireless signal to a remote receiver which may in turn result in an auditory signal, visual signal, tactile signal or other sensory signal and/or combinations thereof.

Various sensors may be used, including inductive, capacitive, ultra sonic, optical, moisture, humidity (e.g., MVTR), pH, biological, chemical, mechanical, temperature, electromagnetic and combinations thereof, as described and illustrated (see FIGS. 5A-7C) in the '463 and '456 Apps.

Figure 2:
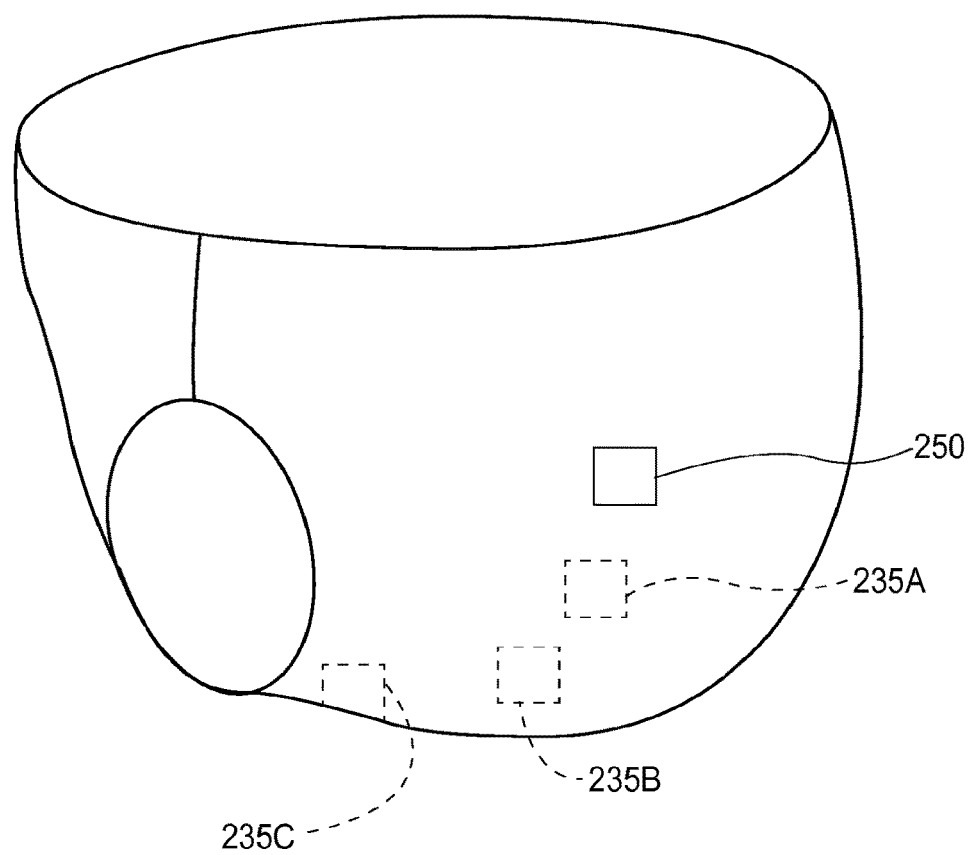
FIG. 2 illustrates a perspective view of a pant-type absorbent article with a sensor in the front, according to embodiments of the present disclosure.

The sensor system may include one or more transmitters. A transmitter is a device that sends electromagnetic waves carrying messages or signals, for instance, one or more of the sensor elements (e.g., 470, 471, or 472) may comprise a transmitter. Alternatively, a transmitter may be removably fixed to the absorbent article or to an auxiliary article such that it is in contact or in communication with the sensor elements, as described in the '463 and '456 Apps., and as illustrated in FIG. 2.

Regarding the safety concerns associated with transmitters, proposed safety guidelines for exposure to non-ionizing radiation include thresholds for power density, electric field strength, and Electromagnetic Field (EMF) exposure. Under some hypotheses, EMF exposure is particularly relevant with respect to Ultra High Frequency (UHF, 300 MHz to 3 GHz) and Super High Frequency (SHF, 3 GHz to 30 GHz) radio frequencies. Each of these measures can be calculated to provide a reasonable approximation of the exposure generated by transmitters as described herein, based on the power of the outgoing signals and the distance from the transmitter to the target (e.g., the sensor(s) or the mobile device(s)). Watts are the units used to describe the amount of power generated by a transmitter. Microvolts per meter ($\mu$V/m) are the units used to describe the strength of an electric field created by the operation of a transmitter. A particular transmitter that generates a constant level of power (Watts) can produce electric fields of different strengths ($\mu$V/m) depending on, among other things, the type of transmission line and antenna connected to it. Because it is the electric field that causes interference to authorized radio communications, and because particular electric field strengths do not directly correspond to a particular level of transmitter power, the emission limits of, for example, short range devices and broadcasting transmitters, are specified by field strength.

Although the precise relationship between power and field strength can depend on a number of additional factors, the relationship can be approximated based on the following formula:

$$\frac{PG}{4d^2} = \frac{E^2}{120}$$

where P is transmitter power in Watts, G is the numerical gain of the transmitting antennae relative to an isotropic source, d is the distance of the measuring point from the electrical center of the antenna in meters, and E is the field strength in Volts/meter. As to the denominators, 4d2 is the surface area of the sphere centered at the radiating source whose surface is d meters from the radiating source, and 120 is the characteristic impedance of free space in Ohms. Using this equation, and assuming a unity gain antenna (G=1) and a measurement distance of 3 meters (d=3), a formula for determining power given field strength can be developed:

$$P=0.3E^2$$

where P is the transmitter power (EIRP) in Watts and E is the field strength in Volts/meter. The following expression relates power flux-density in dB(W/m$^2$) with field strength in dB($\mu$V/m):

$$E=S+145.8$$

where E is field strength in dB($\mu$V/m) and S is power flux-density in dB(W/m$^2$).

The maximum safe level of exposure is a matter of ongoing investigation. Extremely high exposure to electromagnetic radiation is known to cause heating, and the thermal effects in turn can influence biological tissues in undesirable ways. However, it is unclear whether exposures unassociated with thermal effects are themselves harmful, and if so, at what levels.

Based on the information available today, for continuous monitoring, it may be desirable to limit the average maximum power density of any transmitter on the wearer to less than 10 mW/cm$^2$ (milliwatts per square centimeter). This limit is based on studies on healthy adult humans, and so different limits may be desirable for infants, children, or adults. Thus, it may be desirable to limit the average maximum power density of the transmitter on the wearer to no more than 500 $\mu$W/cm$^2$ (microwatts per square centimeter), or no more than 50 $\mu$W/cm$^2$, or even no more than 20 $\mu$W/cm$^2$. It may be desirable to limit the average maximum energy density of the transmitter on the wearer to no more than 1 mW hr/cm$^2$ (milliwatt-hour per square centimeter) for interrupted or modulated electromagnetic radiation. Each of these averages is taken over any possible six minute (0.1 hour) period.

In the embodiment illustrated by FIG. 2, the transmitter 250 may not send any signals to a remote device until a sensor 235 is triggers it or until a sensor changes status. This can be referred to as a sensor gate. The transmitter may comprise a monitoring function wherein the transmitter assesses the state of the sensor either continuously or intermittently. Once the transmitter determines a change in state the transmitter becomes active and transmits a signal to a receiver. The transmitter may operate at two or more distinct power levels, a first lower power level during the assessment operation and a second higher power level during the transmission operation. It should be understood that in either operation it may be desirable to minimize the duration of the power on cycle in order to minimize exposure of the wearer to electromagnetic exposure.

Alternatively, transmitter 250, which may be located in the font or the back, may send a low energy signal (an average maximum energy density less than 1 mW hr/cm$^2$) periodically to check the status of a first sensor 235A and will not transmit a higher energy signal (an average maximum energy density greater than 1 mW hr/cm$^2$) to a remote device (e.g., a phone, a monitor, etc.) until the sensor status changes from a first status to a second status. For instance, transmitter 250 may check the status of sensor 235A every 1, 5, 15, 30, 150 or 300 seconds. If after the first check of sensor 235A, the status is A (e.g., moisture or temperature threshold not exceeded), the transmitter will check again in the programmed amount of time. In this situation, the sensor gate of 235A is closed. If the status of sensor 235 is status B (e.g., moisture or temperature threshold is exceeded, or presence of a certain chemical is detected—like a byproduct of urine), then the transmitter may send a signal to the mobile device. In this situation, the sensor gate of 235A is open.

Before the transmitter 250 sends a signal to the mobile device, it may first check the status of second sensor 235B. If the second sensor 235B has changed from status C to status D, transmitter 250 may send a signal to the mobile device.

Transmitter 250 may activate periodically in order to check the status of sensor 235 and will not transmit a signal to a remote device (e.g., a phone, a monitor, etc.) until the sensor status changes. For instance, transmitter 250 may check the status of sensor 235 every 1, 5, 15, 30, 150 or 300 seconds. If after the first check of sensor 235, the status is status unchanged from previous, the transmitter will check again in the programmed amount of time. If the status of sensor 235 is status has changed from previous, then the transmitter can send a signal to the receiver or mobile device.

Sensors A, B, and C may be placed longitudinally inward of one another such that they are disposed in zones of that may indicative of how wet the absorbent article is. For instance, sensor A may be placed at the common initial pee point, but sensor B may be placed in a zone outside of the zone of an initial gush, but may be disposed in a zone commonly wetted by a second gush. Sensor C may be disposed in a zone outside of a the zone of the initial or second gush, but may be placed in a zone commonly wetted by a third gush and may signify that the absorbent article is out of capacity or is near the end of capacity.

As illustrated in FIG. 4, sensors 433 and 437 may be disposed proximate to the leg cuffs 480. The sensors 433 and 437 may alternatively be placed on or between the layers of the leg cuff. Examples of acceptable cuffs 480 are disclosed in U.S. Ser. No. 13/457,521, filed Apr. 27, 2012, including the configurations disclosed by FIGS. 8a-t of the '521 App. The leg cuffs may be a two-piece cuff. And, the cuff may be joined to the backsheet with a no leak bead that runs along the entire longitudinal length of the cuff and/or the backsheet film.

To keep the emissions of energy as low as possible, the transmitter may not check the status of the second or third sensors 235B or C until the status of the first sensor changes from status A to status B.

The transmitter may check the sensor(s) more periodically after a certain period of time passes. For instance, in a system that monitors for a wet diaper, the transmitter may check the sensor every 15 seconds until a change in status then it may check the sensor at a longer interval for a set period of time for example every minute for 90 minutes and then every 30 seconds for another 90 minutes and then every 15 seconds until another change in status is perceived. The transmitter may also alter its checking frequency based on the wearer's event history (e.g., the transmitter may take into consideration the time of day, the day of the week, and the wearer's previous urination events). The user may also manually override the periodic sensor polling by opening an application on the remote device such as a mobile phone. The override could come in the form of opening the application to automatically check the status or by pressing a button on the remote device or the transmitter in order to check the current status. The application interface may also provide information such as: time of last diaper change, calendar showing frequency of changes, baby development characteristics (e.g., time between loading events), time of last application check, and/or recommendations on diaper sizes, supporting products, etc.

The transmitter as illustrated in FIG. 2 may only emit enough energy (from 20 to 500 μW/cm$^2$) to get a signal to a remote device (that has a second transmitter) that is one or several rooms away in a residence (e.g., an area of from about 50 to about 1000 feet). The transmitter may only emit this energy for a short time (e.g., less than a second, for 2, 3, 4, 5, 10, or 15 seconds). The remote device may then send (via the second transmitter) a stronger (an average maximum energy density greater than 1 mW hr/cm$^2$) signal to a cell tower or other means of service.

Transmitters on or in absorbent articles of the present disclosure may be programmed to emit no more than an average maximum power density of 20 μW/cm$^2$ per hour and no more than an average maximum power density of 500 μW/cm$^2$ per day.

Figure 5:
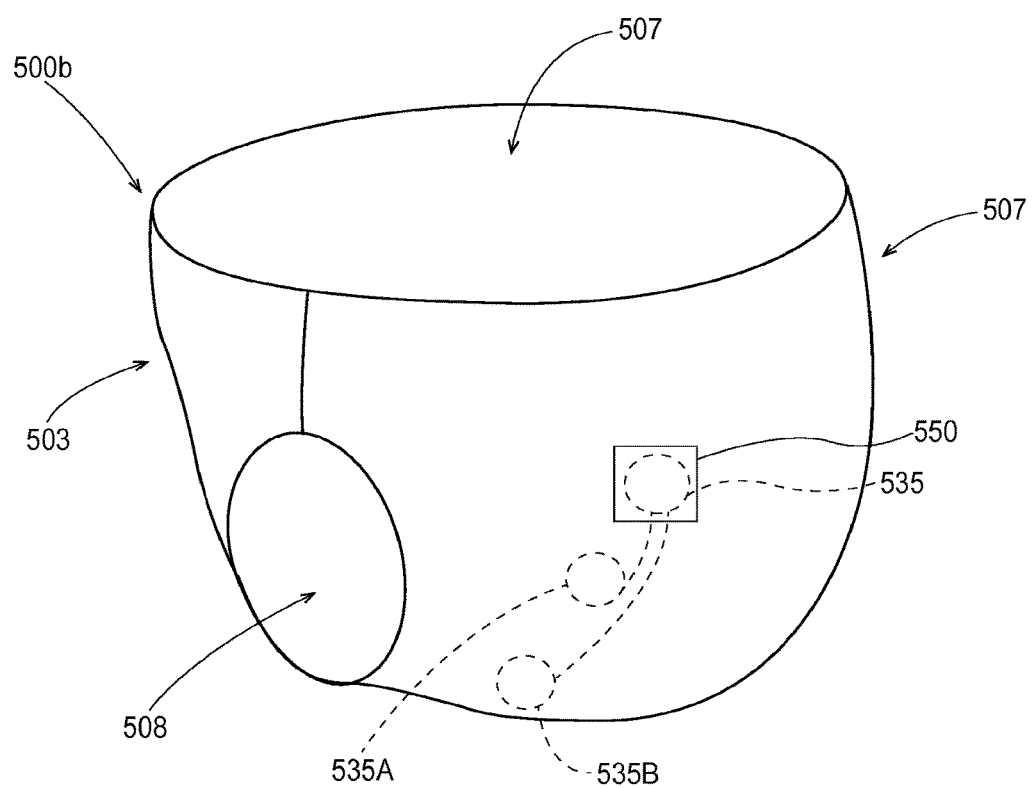
FIG. 5 illustrates a perspective view of a pant-type absorbent article with a sensor comprising leads according to embodiments of the present disclosure.

In another embodiment, illustrated in FIG. 5, the sensor 535 may comprise a first lead 535A and a second lead 535B. The leads 535A and B may detect the same stimulus (e.g., moisture) or different stimuli. In one embodiment, the first lead 535A detects moisture and the second lead 535B detects urea. Sensor 535 may comprise 3, 4, 5, 10, or 20 leads.

The leads 535A and B may be disposed at different longitudinal positions. One advantage of such positioning, when each of the leads detects moisture, is to have a means of sensing different capacities of the core and/or sensing the number of insults in the article. Such information may be helpful for utilizing the fullest capacity of the article, thus decreasing waste by changing the absorbent article earlier than needed or waiting too long to change the article. Sensor placement could also help differentiate between bowel movements ("BM") and fullness of the article. For example, a BM sensor could be placed in a pre-determined position in the back of the diaper and a fullness sensor could be placed in a pre-determined position in the front of the diaper. Additionally, this information may be helpful for training toddlers and also for decreasing bed sores of incontinent adults that are being cared for by others (e.g., a nursing home institution). The information of what is happening in the absorbent article can become more sophisticated with the use of more leads and/or more sensors.

The transmitter 550 may check the status of sensor 535 every 1, 5, 15, 30, 150 or 300 seconds. If after the first check of sensor 535, the status is A-A (i.e., both leads have not detected their stimuli), the transmitter will check again in the programmed amount of time. If the status of sensor 535 is status A-B or B-A or B-B (e.g., moisture or temperature threshold is exceeded by one or both of the leads), then the transmitter may send a signal to the remote or mobile device.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sensor system for detecting a property of or within an absorbent article, comprising:
    an absorbent article comprising a front region, a back region, and a crotch region, a transverse axis and a longitudinal axis; the absorbent article further comprising an elongate housing comprising a first sensor and a second sensor;
    a first transmitter;
    wherein the elongate housing is disposed such that each of the first and second sensors are disposed forward of the transverse axis of the absorbent article;
    wherein no sensor of the sensor system and no portion of the housing is disposed rearward of the transverse axis;
    wherein at least one of the first and second sensors overlaps with the longitudinal axis;
    wherein the elongate housing is disposed along a longitudinal axis of the absorbent article, and wherein the elongate carrier layer is disposed on a garment-facing, exterior surface of the absorbent article, and wherein the elongate housing comprises at least one of hooks and loops;
    wherein the first sensor has a first status and is capable of changing to a second status;
    wherein the second sensor has a third status and is capable of changing to a fourth status;
    wherein at least one of the first and second sensors are capable of sensing a color change through the garment-facing, exterior surface of the absorbent article;
    wherein the first transmitter is capable of transmitting a signal when a change in status of the first sensor from the first status to the second status has occurred;
    wherein the first transmitter is capable of transmitting a signal when a change in status of the second sensor from the third status to the fourth status has occurred;
    wherein the first transmitter is capable of operating at a first power level during an assessment operation and a second power level, higher than the first power level, during a transmission operation.

2. The sensor system of claim 1, wherein the sensor system comprises a second transmitter.

3. The sensor system of claim 2, wherein the first transmitter is capable of sending a signal to a remote device that comprises the second transmitter.

4. The sensor system of claim 3, wherein the first transmitter is programmed to send the signal to the remote device after the first sensor has the second status.

5. The sensor system of claim 2, wherein the first transmitter is programmed to send the signal to the remote device after the second sensor has the fourth status.

6. The sensor system of claim 1, wherein the first transmitter is capable of being manually overridden by the user with a mobile application interface either from an application opening or by manually pressing a button on an application graphical user interface ("GUI") to check a current status of the first and/or second sensors.

7. The sensor system of claim 1, wherein the first sensor is disposed in the front region.

8. The sensor system of claim 5, wherein the second sensor is disposed in the front region, laterally outboard of the first sensor.

9. The sensor system of claim 1, further comprising a graphic for properly placing the first and second sensors.

10. The sensor system of claim 1, wherein the second and fourth status occur due to different stimuli.

11. The sensor system of claim 10, wherein at least one of the different stimuli is vapor.

12. The sensor system of claim 10, wherein at least one of the different stimuli is temperature.

13. The sensor system of claim 10, wherein at least one of the different stimuli is mechanical.

14. The sensor system of claim 13, where in the mechanical stimulus is selected from one or a combination of strain, stress, and mechanical failure.

15. The sensor system of claim 10, wherein at least one of the different stimuli is acidity/basicity ("pH").

16. The sensor system of claim 10, wherein at least one of the different stimuli is a biological element.

17. The sensor system of claim 16, wherein the biological element is blood, biomarkers, and proteins.

18. The sensor system of claim 10, wherein at least one of the different stimuli is a chemical.

19. The sensor system of claim 13, wherein the chemical/analyte is selected from one or a combination of ammonia, urea, chloride, sodium, potassium, sugar, and creatinine.

20. A sensor system for detecting a property of or within an absorbent article, comprising:
    an absorbent article comprising a front region, a back region, and a crotch region, a transverse axis and a longitudinal axis; the absorbent article further comprising an elongate housing comprising a first sensor and a second sensor;
    a first transmitter;
    wherein the elongate housing is disposed such that each of the first and second sensors are disposed forward of the transverse axis of the absorbent article;
    wherein the elongate housing is disposed along a longitudinal axis of the absorbent article, and wherein the elongate housing is disposed on a garment-facing, exterior surface of the absorbent article, and wherein the elongate housing comprises at least one of hooks and loops;

wherein at least one of the first and second sensors are capable of sensing a color change through the garment-facing, exterior surface of the absorbent article;

wherein the first transmitter is capable of transmitting a signal when the at least one of the first and second sensors senses a color change through the garment-facing, exterior surface of the absorbent article;

wherein the first transmitter is capable of operating at a first power level during a n assessment operation and a second power level, higher than the first power level, during a transmission operation; and a graphic for properly placing the elongate housing on the garment-facing, exterior surface of the absorbent article, such that neither the elongate housing nor the first and second sensors are in direct contact with the wearer.

21. The sensor system of claim 1, wherein the first transmitter emits for less than 10 seconds when signaling to a remote device.

22. The sensor system of claim 1, wherein the first transmitter emits for less than 5 seconds when signaling to a remote device.

23. The sensor system of claim 1, wherein the first transmitter emits for less than 2 seconds when signaling to a remote device.

24. The sensor system of claim 1, wherein the first transmitter emits an average of less than 500 $\mu W/cm^2$ per hour.

25. The sensor system of claim 1, wherein the first transmitter emits an average of less than 50 $\mu W/cm^2$ per hour.

26. The sensor system of claim 1, wherein the first transmitter emits an average of less than 20 $\mu W/cm^2$ per hour.

27. A sensor system for detecting a property of or within an absorbent article, comprising:

an absorbent article comprising a front region, a back region, and a crotch region, a transverse axis and a longitudinal axis; the absorbent article further comprising an elongate housing comprising a first sensor and a second sensor;

a first transmitter;

wherein the elongate housing is disposed such that each of the first and second sensors are disposed forward of the transverse axis of the absorbent article;

wherein no sensor of the sensor system and no portion of the housing is disposed rearward of the transverse axis;

wherein at least one of the first and second sensors overlaps with the longitudinal axis;

wherein the elongate housing is disposed along a longitudinal axis of the absorbent article, and wherein the elongate carrier layer is disposed on a garment-facing, exterior surface of the absorbent article, and wherein the elongate housing comprises at least one of hooks and loops;

wherein the first sensor has a first status and is capable of changing to a second status;

wherein the second sensor has a third status and is capable of changing to a fourth status;

wherein at least one of the first and second sensors are capable of sensing a color change through the garment-facing, exterior surface of the absorbent article;

wherein the first transmitter is capable of transmitting a signal when a change in status of the first sensor from the first status to the second status has occurred;

wherein the first transmitter is capable of transmitting a signal when a change in status of the second sensor from the third status to the fourth status has occurred;

wherein the first transmitter emits non-continuously when signaling to a remote device; and wherein the first transmitter is capable of operating at a first power level during an assessment operation and a second power level, higher than the first power level, during a transmission operation.

28. A sensor system for detecting a property of or within an absorbent article, comprising:

an absorbent article comprising a front region, a back region, and a crotch region, a transverse axis and a longitudinal axis; the absorbent article further comprising an elongate housing comprising a first sensor and a second sensor;

a first transmitter;

wherein the elongate housing is disposed such that each of the first and second sensors are disposed forward of the transverse axis of the absorbent article;

wherein no sensor of the sensor system and no portion of the housing is disposed rearward of the transverse axis;

wherein the elongate housing is disposed along a longitudinal axis of the absorbent article, and wherein the elongate carrier layer is disposed on a garment-facing, exterior surface of the absorbent article;

wherein the first sensor has a first status and is capable of changing to a second status;

wherein the second sensor has a third status and is capable of changing to a fourth status;

wherein at least one of the first and second sensors are capable of sensing a color change through the garment-facing, exterior surface of the absorbent article;

wherein the first transmitter is capable of transmitting a signal when a change in status of the first sensor from the first status to the second status has occurred;

wherein the first transmitter is capable of transmitting a signal when a change in status of the second sensor from the third status to the fourth status has occurred;

wherein the first transmitter is capable of operating at a first power level during an assessment operation and a second power level, higher than the first power level, during a transmission operation; and wherein the first transmitter is capable of being manually overridden by the user with a mobile application interface either from an application opening or by manually pressing a button on an application graphical user interface ("GUI") to check a current status of the first and/or second sensors.

* * * * *